United States Patent [19]
Andrews et al.

[11] Patent Number: 5,437,621
[45] Date of Patent: * Aug. 1, 1995

[54] MEDICAL DRESSING OF A MULTILAYERED MATERIAL

[75] Inventors: Warren L. Andrews, Chicago; C. Robert Hammett, Palatine, both of Ill.

[73] Assignee: Marmon Holdings, Inc., Chicago, Ill.

[ * ] Notice: The portion of the term of this patent subsequent to Jul. 12, 2011 has been disclaimed.

[21] Appl. No.: 3,359

[22] Filed: Jan. 12, 1993

Related U.S. Application Data

[63] Continuation-in-part of Ser. No. 978,556, Nov. 19, 1992, Pat. No. 5,328,449.

[51] Int. Cl.$^6$ ............................................. A61F 13/00
[52] U.S. Cl. ............................................. 602/42; 602/21; 602/62; 602/63; 602/64; 2/16; 2/21
[58] Field of Search .................. 602/21, 41, 42, 43, 602/47, 58, 59, 62, 63, 64; 604/292, 306, 370, 372, 383, 391; 2/16, 21, 19, 159, 161 A, 164; 128/888; 606/214, 215, 216

[56] References Cited

U.S. PATENT DOCUMENTS

| | | | |
|---|---|---|---|
| 3,249,109 | 5/1966 | Maeth et al. | 602/49 |
| 3,307,545 | 3/1967 | Surowitz | 128/156 |
| 3,384,083 | 5/1968 | Cozza et al. | 604/292 |
| 3,416,526 | 12/1968 | Yeremian | 602/59 |
| 3,521,631 | 7/1970 | Gardner et al. | 602/42 |
| 4,360,015 | 11/1982 | Mayer | 602/47 |
| 4,430,759 | 2/1984 | Jackrel | 2/159 |
| 4,499,896 | 2/1985 | Heinecke | 602/47 |
| 4,783,857 | 11/1988 | Suzuki et al. | 2/167 |
| 4,867,150 | 9/1989 | Gilbert | 602/47 |
| 5,086,763 | 2/1992 | Hathman | 128/888 |
| 5,117,509 | 6/1992 | Bowers | 2/161 A |
| 5,328,449 | 7/1994 | Andrews et al. | 604/292 |

FOREIGN PATENT DOCUMENTS 2268504 11/1975 France ............................ 606/215

Primary Examiner—Paul Prebilic
Attorney, Agent, or Firm—Jon Carl Gealow; Keck, Mahin & Cate

[57] ABSTRACT

A medical dressing for covering a wound, lesion, burn or similar injury is disclosed. The dressing comprises a material having at least three layers comprising: (a) a first inner layer which comprises a porous polyethylene film which enables moisture to be wicked away from the injury; (b) a second middle layer comprising an absorbent material for absorbing the moisture from the first layer; and (c) a third outer layer comprising a flexible, water-proof and breathable material.

6 Claims, 2 Drawing Sheets

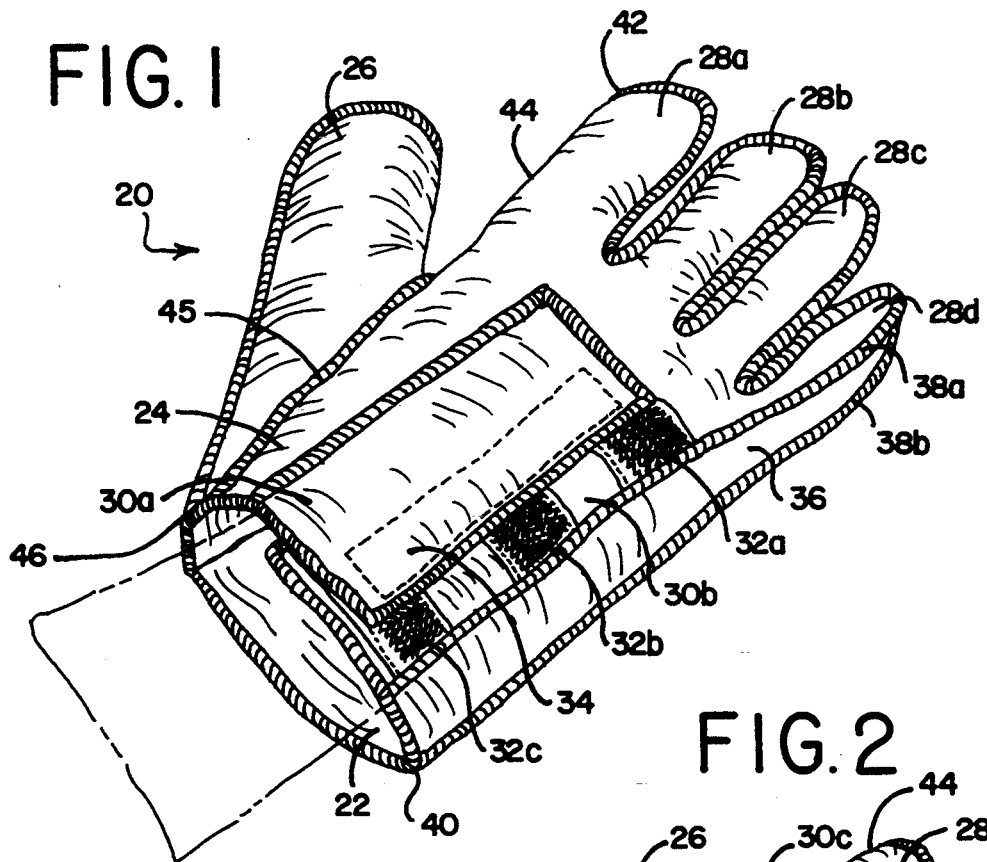
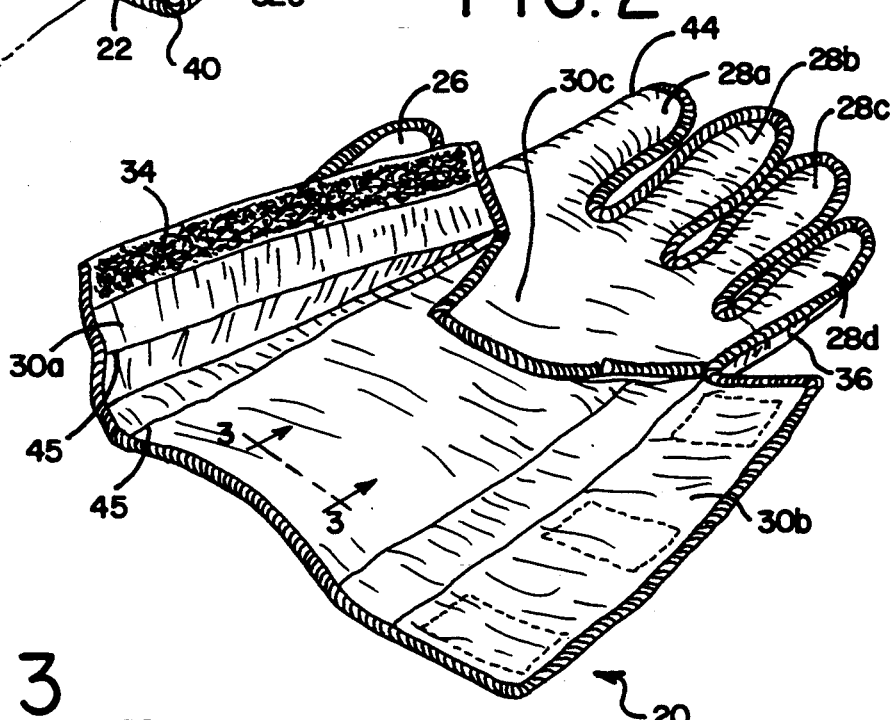
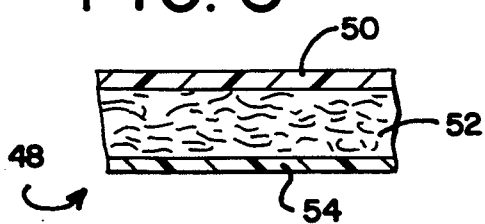

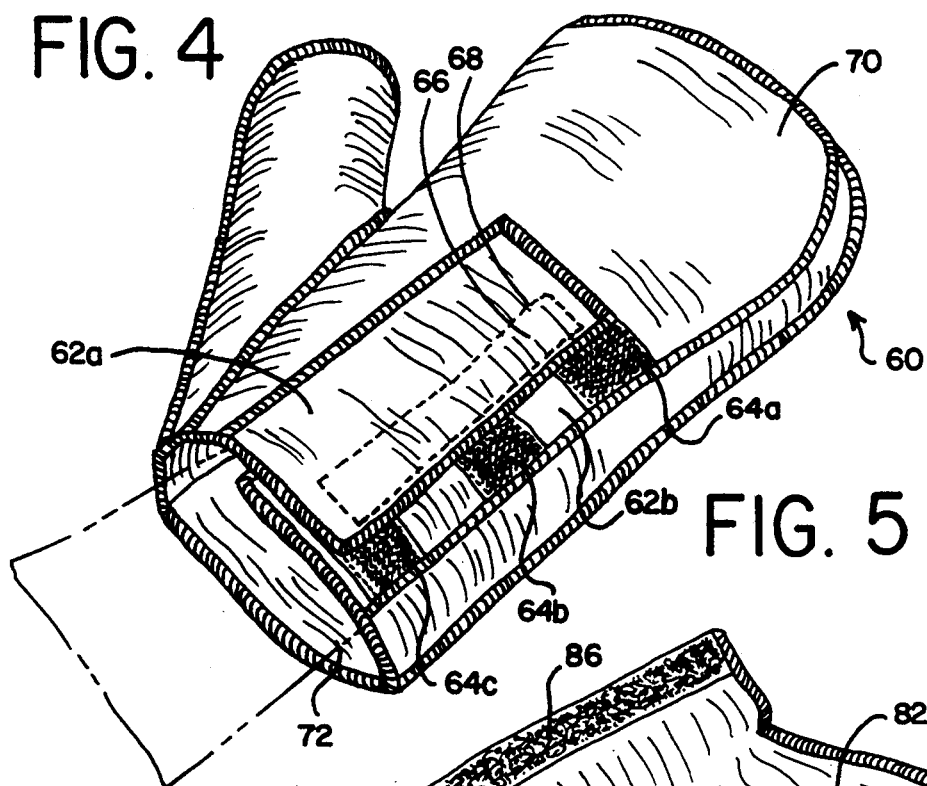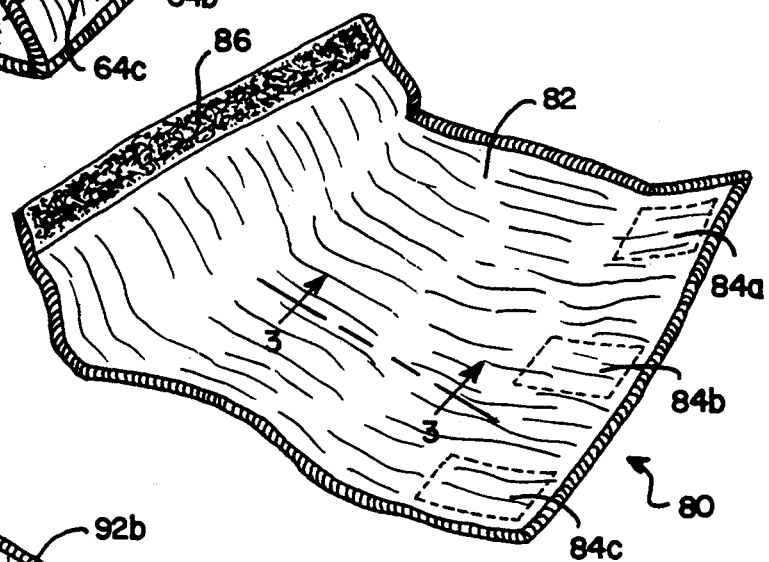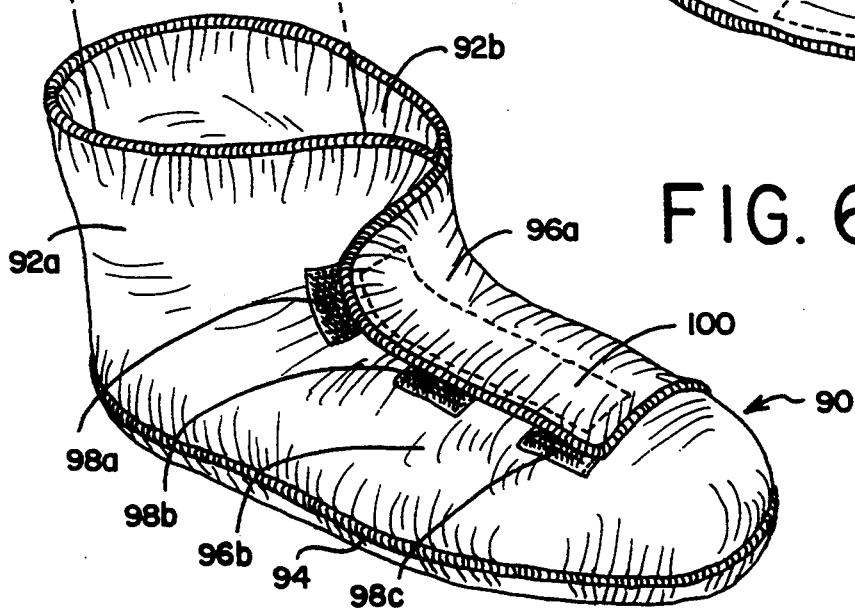

MEDICAL DRESSING OF A MULTILAYERED MATERIAL

This application is a continuation-in-part of commonly assigned, United States patent application Ser. No. 07/978,556, filed on Nov. 19, 1992 now U.S. Pat. No. 5,328,449.

FIELD OF THE INVENTION

This invention relates to medical dressings or bandages for covering a wound, lesion, burn or similar injury, and particularly to medical dressings comprised of a multi-layered material for protecting and promoting the healing of such injuries.

BACKGROUND

Patients having wounds, lesions, burns or other similar trauma or injury require special treatment to preserve the function of the area of injury while promoting healing of the injury. For example, according to Smith et al., Burns 14,(5): 405–408, (1988), six principles have been formulated for the care of burned hands to achieve the return of optimal function, including: (1) to do no harm; (2) to maintain vascularity; (3) to prevent infection; (4) to obtain wound closure; (5) to preserve and regain motion; and (6) to obtain optimal functional rehabilitation. Many of the same principles would also apply to other body sites and other types of injuries.

Prior art medical dressings have not been manufactured from a material which provides optimal healing and function of the injured area. In addition, prior medical dressings have not provided a complete bandage or dressing which enables easy application, inspection of the underlying injury and removal of the dressing. Further, while various materials and methods of manufacturing medical dressings or bandages are known in the art, these materials and methods do not generally provide a versatile medical dressing for covering difficult body sites such as an injured hand, foot or other area of the body which is not easily protected by standard bandages or dressings.

For example, in one method for dressing a hand injury, prior art medical dressings or gloves are made by cutting two complimentary, flat, top and bottom hand-shaped sections and sewing them together around the perimeter, leaving an opening at the wrist end. One problem with using this type of glove to cover an injured hand is that the glove does not provide for an easy and comfortable insertion or removal of the hand. Further, gloves of this construction do not allow comfortable movement of the injured hand which could be harmful to return of optimal hand function.

Other prior art medical gloves or hand dressings have attempted to avoid the above-described problems by enlarging the overall size of the glove so that the opening is wide enough to insert the hand and provide a loose fit. However, one problem with such an oversized glove construction is that the loose fit causes the glove or dressing to slip off the hand. Also, the oversized glove construction may cause loss of hand coordination and manipulation skills. For example, the excess material of an over-sized glove may make it difficult to handle small objects such as writing instruments or eating utensils.

It is therefore an object of the present invention to provide a versatile medical dressing for covering many different shapes and sizes of injuries including difficult-to-cover body sites such as a hand or foot. It is another object to provide a medical dressing which prevents adhesion of the dressing to an injury and enables optimal healing and function of an injured area of the body. It is yet another object to provide a medical dressing which enables a comfortable fit and easy application and removal of the dressing. It is another object to provide a medical dressing which facilitates inspection and treatment of an underlying injury.

In one embodiment, it is an object to provide a medical glove or mitten for covering or dressing hands having wounds, lesions, burns or similar injuries, which facilitates easy insertion and removal of the hand and a comfortable fit, while still enabling a simple glove or mitten construction. In another embodiment, it is an object to provide a boot for covering an injured foot. It is a further object to provide a medical dressing made from a unique material which facilitates function, rehabilitation and healing of an area of the body which has been burned, wounded or subjected to similar trauma or injury.

SUMMARY OF THE INVENTION

The above objects are accomplished by the present invention which is a medical dressing for covering wounds, lesions, burns or similar injuries comprising a material having at least three layers comprising:
 (a) a first inner layer which will contact the injury comprising a porous polyethylene film which enables moisture to be wicked away from the injury and is non-adherent so the dressing will not stick to the injury;
 (b) a second middle layer comprising an absorbent material for absorbing the moisture from the first layer; and
 (c) a third outer layer comprising a flexible, waterproof and breathable material.

In one preferred embodiment, the medical dressing further comprises adjustable opening and closure means for easy application and removal of the medical dressing and for adjustable fitting the medical dressing to the area of injury.

In another preferred embodiment, the medical dressing comprises a medical glove for covering wounds, lesions, burns or similar injuries to a hand comprising a back portion, a palm portion and thumb and finger portions for covering the hand. The medical glove has adjustable opening and closure means for easy insertion and removal of the hand and for adjustable fitting the glove to the hand. The glove also comprises a material having at least three layers comprising:
 (a) a first inner layer which will come into contact with the hand comprising a porous polyethylene film which enables moisture to be wicked away from the hand and is non-adherent so the glove will not stick to the wound;
 (b) a second middle layer comprising an absorbent material for absorbing the moisture from the first layer; and
 (c) a third outer layer comprising a flexible, waterproof, breathable material.

In another embodiment, the medical dressing comprises a mitten for covering a hand injury where a glove may not be the dressing of choice, such as in the case of pediatric applications. In still another embodiment, the medical dressing comprises a boot or foot wrap for covering an injury to a foot.

BRIEF DESCRIPTION OF THE DRAWINGS

FIG. 1 is a perspective view of one embodiment of a medical dressing according to the invention, which shows a back side of a medical glove with adjustable opening and closure means in a closed position;

FIG. 2 is another perspective view of the glove of FIG. 1, showing the adjustable opening and closure means in an open position;

FIG. 3 is a sectional view along lines 3—3 of FIGS. 2 and 5;

FIG. 4 is a perspective view of another embodiment of a medical dressing according to the invention in the form of a mitten with adjustable opening and closure means in a closed position;

FIG. 5 is a perspective view of a medical dressing according to the invention in the form of a medical wrap with adjustable opening and closure means in an open position; and FIG. 6 is a perspective view of another embodiment of a medical dressing according to the invention in the form of a boot with adjustable opening and closure means in a closed position.

DETAILED DESCRIPTION OF THE INVENTION

As used herein, "injured site" or "injury" means a wound, lesion, burn or other trauma to a human or animal body site which may require a medical dressing, cover or bandage. As used herein, "medical dressing" means a covering or bandage for wounds, lesions, burns or other trauma to a human or animal body site.

The medical dressing of the present invention comprises a unique material having at least three layers which enables optimal healing of an injured site. This unique material 48 (FIG. 3) comprises a first, inner layer 50 which will contact the injured site or any medicament or material applied to the injury. This inner layer 50 comprises a porous, non-adherent polyethylene film which enables moisture to be wicked away from the injury and prevent adhesion of the dressing to the wound.

In a preferred embodiment, the inner layer 50 comprises a porous polyethylene film having a thickness of about 3.5–5.0 mils. One example of a most preferred material for the inner layer 50 is a polyethylene film sold by Applied Extrusion Technologies, Middletown, Del., under the name P530 Delnet. This material has a thickness of about 3.8–4.8 mils, a boss count (MD) of about 18–24 ct/in, a boss count (CD) of about 32–40 ct/in and a yield of about 25–35 syd/lb.

The inner layer 50 is hydrophobic and facilitates wicking of any liquid discharge from an injury to the middle layer 52 of the medical dressing, which results in a drier surface adjacent the skin. The inner layer 50 also prevents adhesion of the dressing to the wound. In use of the dressing, when an injury has any fluid discharge, the fluid will pass through the inner layer 50, saturate the middle layer 52 and migrate by wicking toward the outer layer 54, leaving a relatively dry surface at the hydrophobic inner layer 50 adjacent the injury.

The second, middle layer 52 comprises an absorbent material for absorbing any moisture from the inner layer 50. In a preferred embodiment, the middle layer 52 comprises an absorbent needle-punched, non-woven rayon such as a four ounce per square yard needle-punched, non-woven rayon. Other suitable absorbent materials include creped cellulose wadding, an airfelt of airlaid pulp fibers, cotton or other well known absorbent materials suitable for use in wound dressings.

A third, outer layer 54 comprises a flexible, waterproof and breathable material which protects the injury from exposure to contaminants from the outer atmosphere, while preventing leakage of any moisture from the injury. In a preferred embodiment of the invention, the outer layer 54 comprises a waterproof, breathable polyurethane film of an approximately 0.5–1.5 mil thickness and preferably about a 1 mil thickness. Other suitable waterproof, breathable outer layer materials include polypropylene or polyethylene such as a low density, opaque polyethylene film, or other waterproof and breathable materials suitable for use in wound dressings.

The layers 50, 52, 54 are provided as one complete wound dressing material 48 and can be secured to one another in any convenient manner; for example, the layers can be sewn together, adhesively secured or bonded with heat and pressure or sonics.

The medical dressing material 48 comprising the three layers described above can be provided in many forms to enable a convenient and easy to use medical dressing. For example, the medical dressing material 48 may be provided in conveniently sized rolls such as about two to about three-inch widths which are provided on a roll of suitable length such as about five feet in length. In this manner, the desired medical dressing length can simply be cut from the roll. Also, the medical dressing of the invention may be provided in sheets of a desired size and shape such as rectangular or square-shaped sheets. For example, in one embodiment, the medical dressing can comprise a rectangular or square sheet of about four to about five inches in width and/or length. In another embodiment, the medical dressing can comprise an approximately eight inch by approximately ten inch rectangular sheet.

In one preferred embodiment, the medical dressing further comprises adjustable opening and closure means for easy application and removal of the medical dressing and for adjustable fitting the medical dressing to the area of injury. Such opening and closure means may be provided for many different shapes and sizes of medical dressings according to the invention.

As shown in FIGS. 1 and 2, in one preferred embodiment, a medical dressing in accordance with the present invention may be provided in the form of a medical glove 20 which comprises a palm portion 22, a back portion 24, a thumb portion 26, and finger portions 28a–d. The glove 20 further comprises adjustable opening and closure means which, in the preferred embodiment, comprises at least two adjustable opening and closure flaps 30a and b. The adjustable opening and closure flaps 30a and b have adjustable fastening means, for example, hook and loop fasteners such as horizontal Velcro strips 32 a–c and vertical mating Velcro strip 34. Other adjustable fasteners which are well known in the art, such as reusable adhesive tab closures used in the disposable diaper industry, may be substituted for the Velcro fasteners, so long as the selected fasteners enable adjustable opening and closing of the glove for various sized hands and a comfortable fit. The adjustable opening and closure means enables easy and comfortable insertion and removal of an injured hand when the adjustable opening and closure means is in an open position (FIG. 2), while also allowing for quick and easy adjustment of a comfortable fit of the medical glove 20 (FIG. 1). The adjustable opening and closure means also enables a treating medical clinician to easily inspect or treat the injured hand.

In the embodiment shown in FIGS. 1 and 2, the adjustable opening and closure means is integral with and forms a portion of the back portion 24 of the glove 20. However, it should be understood that in another preferred embodiment, the adjustable opening and closure means may be integral with and form a portion of the palm portion 22.

The adjustable opening and closure means of the preferred embodiment of the medical glove 20 further comprises an additional flap 30c which tucks under the opening and closure flaps 30a and b to insure complete coverage of the hand, while preventing any exposure of the hand to the atmosphere. Such exposure could cause infection or further trauma to the injured hand.

In order to provide a comfortable fit, in the preferred embodiment of the medical glove 20, the finger portions 28a–d comprise palm-side finger portions which are integral with and form one continuous piece with back portion 24, as shown in FIGS. 1 and 2, and palm-side finger portions (not shown) which are integral with and form one continuous piece with the palm portion 22. The back-side finger portions are an approximate mirror image of the palm-side finger portions. The palm- and back-side finger portions are joined to form finger portions 28a–d by continuous connecting piece 36 which is attached to the back portion 24 and the palm portion 22 at seams 38a and b, respectively. The continuous connecting piece 36 connects the back portion 24 to the palm portion 22 and finger portions 28a–d from the outer wrist end 40 of the glove all the way to the tip 42 of the index finger portion 28a.

At the opposite side of the medical glove below the tip 42 of the index finger portion 28a, a fold 44 is formed where the back portion 24 and palm portion 22 are one continuous piece. The remaining portion of the glove below the fold 44 is completed by thumb portion 26 which connects the back portion 24 and the palm portion 22 of the glove by V-shaped thumb opening seam 45.

Those skilled in the art will readily recognize that the palm, back, finger and thumb portions of the medical glove can be made of other constructions so long as an adjustable opening and closure means is provided for easy and comfortable insertion and removal of a hand, while enabling an adjustable, comfortable fit. Also, the preferred glove construction of the invention will enable optimal protection of an injured hand, while providing for maximum function of the hand such as manipulation of small objects and comfortable movement of the hand. For example, in another embodiment of the invention, a medical glove may comprise a continuous connecting piece such as connecting piece 36 which connects the entire outer perimeter of the glove from one side of the wrist end 40 to the opposite side at wrist end 46 of the thumb portion 26. In yet another embodiment of the invention, the medical glove may comprise adjustable opening and closure means on the palm portion of the glove.

The medical glove of the present invention is constructed of the unique material 48 shown in FIG. 3 and described in detail above having at least three layers which enable optimal healing of an injured hand such as a burned hand. As shown in FIG. 3, this unique material 48 comprises a first, inner layer 50, which will contact the injured hand or any medicament or material previously applied to the hand. This inner layer 50 comprises a porous, non-adherent polyethylene film which enables moisture to be wicked away from the injured hand and prevent adhesion of the glove to the wound.

In a preferred embodiment, the inner layer 50 comprises a porous polyethylene film having a thickness of about 3.5–5.0 mils. One example of a most preferred material for the inner layer 50 is a polyethylene film sold by Applied Extrusion Technologies, Middletown, Delaware, under the trademark P530 Delnet. This material has a thickness of about 3.8–4.8 mils, a boss count (MD) of about 18–24 ct/in, a boss count (CD) of about 32–40 ct/in and a yield of about 25–35 syd/lb.

The inner layer 50 is hydrophobic and facilitates wicking of any liquid discharge from a hand injury such as a burn to the glove's middle layer 52, which results in a drier surface adjacent to the injured hand. The inner layer 50 also prevents adhesion of the glove to the injury. In use of the glove, when an injured hand has any fluid discharge, the fluid will pass through the inner layer 50, saturate the middle layer 52 and migrate by wicking toward the outer layer 54, leaving a relatively dry surface at the hydrophobic inner layer 50 adjacent the hand.

The second, middle layer 52 comprises an absorbent material for absorbing any moisture from the inner layer 50. In a preferred embodiment, the middle layer 52 comprises an absorbent needle-punched, non-woven rayon such as a four ounce per square yard needle-punched, non-woven rayon. Other suitable absorbent materials include creped cellulose wadding, an airfelt of airlaid pulp fibers, cotton or other well known absorbent materials suitable for use in wound dressings.

A third, outer layer 54 comprises a flexible, waterproof and breathable material which protects the hand from exposure to contaminants from the outer atmosphere, while preventing leakage of any moisture from the injured hand. In a preferred embodiment of the invention, the outer layer 54 comprises a waterproof, breathable polyurethane film of approximately 0.5–1.5 mil thickness and preferably a 1 mil thickness. Other suitable waterproof, breathable outer layer materials include polypropylene or polyethylene such as a low density, opaque polyethylene film, or other waterproof breathable materials suitable for use in wound dressings.

The layers 50, 52, 54 can be secured to one another in any convenient manner; for example, the layers can be sewn together, adhesively secured or bonded with heat and pressure or sonics.

The medical glove of the invention has many advantages. First, the glove can be comfortably applied over an injured hand without causing further trauma. Second, the glove can be adjustable fitted to accommodate different sized hands and various types of injuries. Third, the glove enables any fluid discharge to be wicked away from the injured hand which can help prevent infection and promote healing. Fourth, the inner layer of the glove prevents adhesion to the wound. Fifth, the glove enables good manipulation of the hand which is important to the return of full functional skills. Sixth, the glove provides a comfortable protection of the injured hand from the outer environment while preventing leakage of any fluid from the injured hand. Seventh, the glove enables inspection or treatment of a wound without requiring removal of the glove.

FIG. 4 illustrates another embodiment of the medical dressing of the invention. In this embodiment, a mitten 60 is constructed basically as described above for the medical glove 20, except that no individual finger portions are provided. The mitten 60 comprises adjustable opening and closure means having adjustable fastening means which are also constructed as described above for the medical glove 20 of FIGS. 1 and 2. Briefly, the mitten 60 comprises adjustable opening and closure means which, in the preferred embodiment, comprises at least two adjustable opening and closure flaps 62a and b. The adjustable opening and closure flaps 62a and b have adjustable fastening means, for example, hook and loop fasteners such as horizontal Velcro strips 64 a–c and vertical mating Velcro strip 66 on the inner side of opening and closure flap 62a (shown by dotted lines 68 in FIG. 4). Other adjustable fasteners which are well known in the art, such as reusable adhesive tab closures used in the disposable diaper industry, may be substituted for the Velcro fasteners so long as the selected fasteners enable adjustable opening and closing of the mitten for various sized hands and a comfortable fit. The adjustable opening and closure means enables easy and comfortable insertion and removal of an injured hand when the adjustable opening and closure means is in an open position, while also allowing for quick and easy adjustment of a comfortable fit of the mitten 60. The adjustable opening and closure means further enables easy inspection or treatment of an injured hand without necessitating removal of the mitten.

In the embodiment shown in FIG. 4, the adjustable opening and closure means is integral with and forms a portion of the back portion 70 of the mitten 60. However, it should be understood that in another preferred embodiment, the adjustable opening and closure means may be integral with and form a portion of the palm portion 72 of the mitten.

Also, as in the medical glove 20, the adjustable opening and closure means of the preferred embodiment of the mitten 60 may further comprise an additional flap (not shown) which tucks under the opening and closure flaps 62a and b to insure complete coverage of the hand, while preventing any exposure of the hand to the atmosphere.

The medical dressing of the invention may also be conveniently provided as a medical wrap of many convenient sizes and shapes comprising the three-layered material 48 shown in FIG. 3 and described in detail above. As shown in FIG. 5, a medical wrap 80 comprises a rectangular sheet 82 having adjustable opening and closure means for easy application, inspection of an injury and removal of the medical wrap. In this embodiment, the adjustable opening and closure means comprises adjustable fastening means such as horizontal hook and loop fasteners or Velcro strips 84a–c on the outer side of the medical wrap (represented in FIG. 5 by dotted lines) and vertical mating hook and loop fasteners or Velcro strip 86. Other adjustable fasteners which are well known in the art, such as reusable adhesive tabs used in the disposable diaper industry, may be substituted for the hook and loop or Velcro fasteners so long as the selected fasteners enable adjustable opening and closing and comfortable fit of the medical wrap for injuries and body sites of different sizes and shapes. The adjustable opening and closure means also facilitates opening the medical dressing for inspection or treatment of an injury without having to necessarily remove and replace the dressing.

Of course, the medical wrap may be provided in other shapes and sizes than that shown in FIG. 5. For example, in one embodiment, the medical wrap can be provided as an approximately 20 inch by 15 inch rectangle. In another embodiment, the medical wrap can be an approximately 24 inch by 36 inch rectangle.

FIG. 6 shows another embodiment of the medical dressing of the invention. In this embodiment, a medical boot or foot wrap 90 comprises the three-layered material shown in FIG. 3 and described in detail above. The boot further comprises upper portions 92a and b and bottom or sole portion 94. The upper portions 92a and b comprise adjustable opening and closure means having adjustable fastening means which are also constructed basically as described above for the medical glove 20 of FIGS. 1 and 2. In the preferred embodiment, the medical boot comprises at least two adjustable opening and closure flaps 96a and b. The adjustable opening and closure flaps 96a and b have adjustable fastening means, for example, hook and loop fasteners such as horizontal Velcro strips 98 a–c and vertical mating Velcro strip 100 on the inner side of opening and closure flap 96a (shown by dotted lines in FIG. 6). Other adjustable fasteners which are well known in the art, such as reusable adhesive tab closures used in the disposable diaper industry, may be substituted for the Velcro fasteners so long as the selected fasteners enable adjustable opening and closing of the boot for various sized feet and a comfortable fit. The adjustable opening and closure means enables easy and comfortable insertion and removal of an injured foot when the adjustable opening and closure means is in an open position, while also allowing for quick and easy adjustment of a comfortable fit of the boot 90. The adjustable opening and closure means further enables easy inspection or treatment of an injured foot.

In the embodiment shown in FIG. 6, the adjustable opening and closure means is integral with and forms a portion of the upper portions 92a and b (which may be constructed of one continuous piece, as shown, or more than one piece). However, it should be understood that in another preferred embodiment, the adjustable opening and closure means may be integral with and form a portion of the bottom or sole portion 94 of the boot.

The medical dressing of the invention has many advantages. First, the medical dressing promotes healing and prevents infection by providing a dry surface adjacent the injury. Second, the medical dressing of the invention prevents adhesion to the injury. Third, the medical dressing can be adapted to many shapes and sizes to provide a comfortably fitted dressing for injuries of many sizes and shapes and for difficult-to-cover body areas. Fourth, the medical dressing enables comfortable application and removal. Fifth, the dressing allows treatment and inspection of an injury without having to completely remove the dressing. Sixth, the dressing provides protection and breathability of an injury while preventing leakage of fluid from the injury.

While the medical dressing of the invention has been described with respect to specific embodiments, many modifications may be made without departing from the spirit and scope of the invention.

What is claimed is:

1. A medical dressing for covering wounds, lesions, burns or similar injuries comprising a material having at least three layers comprising:
(a) a first inner layer which will contact said injury comprising a porous polyethylene film having a thickness of about 3.5–5.0 mils which enables moisture to be wicked away from the injury and is non-adherent so that the dressing will not stick to the injury;

(b) a second middle layer comprising an absorbent material for absorbing the moisture from the first layer, said second layer comprising an absorbent needle-punched, non-woven rayon;

(c) a third outer layer comprising a flexible, waterproof and breathable polyurethane film which protects the injury from exposure to contaminants from the outer atmosphere while preventing leakage of moisture from the injury; and (d) adjustable opening and closure means for easy application and removal of said dressing, adjustable fitting of said dressing to the injury and easy inspection or treatment of said injury without requiring removal of said medical dressing.

2. The medical dressing of claim 1 wherein said adjustable opening and closure means comprises adjustable fastening means.

3. The medical dressing of claim 2 wherein said adjustable fastening means comprises mating hook and loop fasteners.

4. The medical dressing of claim 1 wherein said medical dressing is formed in the shape of a medical wrap.

5. The medical dressing of claim 1 wherein said medical dressing is formed in the shape of a mitten.

6. The medical dressing of claim 1 wherein said medical dressing is formed in the shape of a boot.

* * * * *